US009226792B2

(12) United States Patent
Bloom

(10) Patent No.: US 9,226,792 B2
(45) Date of Patent: Jan. 5, 2016

(54) DEBRIDEMENT DEVICE AND METHOD

(71) Applicant: Medtronic Advanced Energy LLC, Minneapolis, MN (US)

(72) Inventor: Eliot F. Bloom, Hopkinton, NH (US)

(73) Assignee: MEDTRONIC ADVANCED ENERGY LLC, Minneapolis, MN (US)

( * ) Notice: Subject to any disclaimer, the term of this patent is extended or adjusted under 35 U.S.C. 154(b) by 78 days.

(21) Appl. No.: 13/916,127

(22) Filed: Jun. 12, 2013

(65) Prior Publication Data

US 2013/0331833 A1 Dec. 12, 2013

Related U.S. Application Data

(60) Provisional application No. 61/658,724, filed on Jun. 12, 2012, provisional application No. 61/704,904, filed on Sep. 24, 2012.

(51) Int. Cl.
*A61B 18/12* (2006.01)
*A61B 18/14* (2006.01)
*A61B 18/18* (2006.01)
(Continued)

(52) U.S. Cl.
CPC ....... *A61B 18/1445* (2013.01); *A61B 17/32002* (2013.01); *A61B 18/148* (2013.01); *A61B 18/18* (2013.01); *A61B 2018/0063* (2013.01); *A61B 2018/00208* (2013.01); *A61B 2018/00589* (2013.01); *A61B 2018/00601* (2013.01); *A61B 2218/002* (2013.01)

(58) Field of Classification Search
CPC ..................... A61B 17/32002; A61B 18/1445; A61B 18/148; A61B 18/18; A61B 2018/00208; A61B 2018/00589; A61B 2018/00601; A61B 2018/0063; A61B 2218/002

See application file for complete search history.

(56) References Cited

U.S. PATENT DOCUMENTS 2,888,928 A 6/1959 Seiger
3,223,088 A 12/1965 Barber et al.
(Continued)

FOREIGN PATENT DOCUMENTS

EP 1201196 5/2002
EP 2044893 4/2009
(Continued)

OTHER PUBLICATIONS

Lee et al, Comparative Study on the Long-Term Effectiveness Between Coblation-and Microdebrider-Assisted partial Turbinoplasty, Laryngoscope 116:May 2006 pp. 729-734.
(Continued)

*Primary Examiner* — Michael Peffley
*Assistant Examiner* — Daniel Fowler
(74) *Attorney, Agent, or Firm* — Jeffrey J. Hohenshell

(57) ABSTRACT

Devices, systems and methods for cutting and sealing of tissue such as bone and soft tissue. Devices, systems and methods include delivery of energy including bipolar radiofrequency energy for sealing tissue which may be concurrent with delivery of fluid to a targeted tissue site. Devices include debridement devices which may include a fluid source. Devices include inner and outer shafts coaxially maintained and having cutters for debridement of tissue. An inner shaft may include electrodes apart from the cutter to minimize trauma to tissue during sealing or hemostasis. Devices may include a single, thin liner or sheath for electrically isolating the inner and outer shafts.

15 Claims, 13 Drawing Sheets

(51) Int. Cl.
*A61B 17/32* (2006.01)
*A61B 18/00* (2006.01)

(56) References Cited

U.S. PATENT DOCUMENTS

| | | | |
|---|---|---|---|
| 3,682,130 A | 8/1972 | Jeffers | |
| 3,750,650 A | 8/1973 | Ruttgers | |
| 3,886,944 A * | 6/1975 | Jamshidi | 606/30 |
| 3,955,284 A | 5/1976 | Balson | |
| 3,955,578 A * | 5/1976 | Chamness et al. | 606/47 |
| 4,014,342 A | 3/1977 | Staub et al. | |
| 4,060,088 A | 11/1977 | Morrison, Jr. et al. | |
| 4,174,713 A * | 11/1979 | Mehl | 606/42 |
| 4,195,637 A | 4/1980 | Gruntzig et al. | |
| 4,207,897 A | 6/1980 | Lloyd et al. | |
| 4,248,224 A | 2/1981 | Jones | |
| 4,651,734 A | 3/1987 | Doss et al. | |
| 4,878,493 A | 11/1989 | Pasternak et al. | |
| 4,932,952 A | 6/1990 | Wojciechowicz, Jr. | |
| 4,943,290 A | 7/1990 | Rexroth et al. | |
| 4,950,232 A | 8/1990 | Ruzicka et al. | |
| 4,985,030 A | 1/1991 | Melzer et al. | |
| 4,998,933 A | 3/1991 | Eggers et al. | |
| 5,112,299 A | 5/1992 | Pascaloff | |
| 5,190,541 A | 3/1993 | Abele et al. | |
| 5,195,959 A | 3/1993 | Smith | |
| 5,230,704 A | 7/1993 | Moberg et al. | |
| 5,234,428 A | 8/1993 | Kaufman | |
| 5,254,117 A | 10/1993 | Rigby et al. | |
| 5,275,609 A | 1/1994 | Pingleton et al. | |
| 5,281,215 A | 1/1994 | Milder | |
| 5,282,799 A * | 2/1994 | Rydell | 606/48 |
| 5,330,521 A | 7/1994 | Cohen | |
| 5,334,181 A | 8/1994 | Rubinsky et al. | |
| 5,336,220 A | 8/1994 | Ryan et al. | |
| 5,336,443 A | 8/1994 | Odashima | |
| 5,352,222 A | 10/1994 | Rydell | |
| 5,364,395 A | 11/1994 | West | |
| 5,376,078 A | 12/1994 | Dinger et al. | |
| 5,383,874 A | 1/1995 | Jackson et al. | |
| 5,385,148 A | 1/1995 | Lesh et al. | |
| 5,395,312 A | 3/1995 | Desai | |
| 5,401,272 A | 3/1995 | Perkins | |
| 5,405,348 A | 4/1995 | Anspach et al. | |
| 5,405,376 A | 4/1995 | Mulier et al. | |
| 5,413,556 A | 5/1995 | Whittingham | |
| 5,417,709 A | 5/1995 | Slater | |
| 5,431,168 A | 7/1995 | Webster, Jr. | |
| 5,431,649 A | 7/1995 | Mulier et al. | |
| 5,441,503 A | 8/1995 | Considine et al. | |
| 5,443,463 A | 8/1995 | Stern et al. | |
| 5,445,638 A | 8/1995 | Rydell et al. | |
| 5,460,629 A | 10/1995 | Shlain et al. | |
| 5,490,819 A | 2/1996 | Nicholas et al. | |
| 5,492,527 A | 2/1996 | Glowa et al. | |
| 5,496,271 A | 3/1996 | Burton et al. | |
| 5,505,700 A | 4/1996 | Leone et al. | |
| 5,540,562 A | 7/1996 | Giter | |
| 5,540,708 A | 7/1996 | Lim et al. | |
| 5,542,196 A | 8/1996 | Kantro | |
| 5,542,945 A | 8/1996 | Fritzsch | |
| 5,556,397 A | 9/1996 | Long et al. | |
| 5,560,373 A | 10/1996 | DeSantis | |
| 5,562,702 A | 10/1996 | Huitema et al. | |
| 5,569,243 A | 10/1996 | Kortenbach et al. | |
| 5,569,254 A | 10/1996 | Carlson et al. | |
| 5,573,424 A | 11/1996 | Poppe | |
| 5,595,183 A | 1/1997 | Swanson et al. | |
| 5,599,346 A | 2/1997 | Edwards et al. | |
| 5,605,539 A | 2/1997 | Buelna et al. | |
| 5,609,573 A | 3/1997 | Sandock | |
| 5,620,415 A | 4/1997 | Lucey et al. | |
| 5,620,447 A | 4/1997 | Smith et al. | |
| 5,647,869 A | 7/1997 | Goble et al. | |
| 5,685,838 A | 11/1997 | Peters et al. | |
| 5,688,267 A | 11/1997 | Panescu et al. | |
| 5,697,536 A | 12/1997 | Eggers et al. | |
| 5,712,543 A | 1/1998 | Sjostrom | |
| 5,713,942 A | 2/1998 | Stern | |
| 5,733,280 A | 3/1998 | Avitall | |
| 5,743,903 A | 4/1998 | Stern et al. | |
| 5,766,167 A | 6/1998 | Eggers et al. | |
| 5,792,167 A | 8/1998 | Kablik et al. | |
| 5,797,905 A | 8/1998 | Fleischman et al. | |
| 5,797,960 A | 8/1998 | Stevens et al. | |
| 5,810,764 A | 9/1998 | Eggers et al. | |
| 5,810,802 A | 9/1998 | Panescu et al. | |
| 5,810,809 A * | 9/1998 | Rydell | 606/49 |
| 5,814,044 A | 9/1998 | Hooven | |
| 5,827,216 A | 10/1998 | Igo et al. | |
| 5,836,947 A | 11/1998 | Fleischman et al. | |
| 5,840,030 A | 11/1998 | Ferek-Petric et al. | |
| 5,843,021 A | 12/1998 | Edwards et al. | |
| 5,843,152 A | 12/1998 | Tu et al. | |
| 5,849,023 A | 12/1998 | Mericle | |
| 5,873,855 A | 2/1999 | Eggers et al. | |
| 5,873,886 A | 2/1999 | Larsen et al. | |
| 5,891,142 A | 4/1999 | Eggers et al. | |
| 5,895,355 A | 4/1999 | Schaer | |
| 5,897,553 A | 4/1999 | Mulier | |
| 5,899,915 A | 5/1999 | Saadat | |
| 5,904,681 A | 5/1999 | West, Jr. | |
| 5,913,854 A | 6/1999 | Maguire et al. | |
| 5,916,213 A | 6/1999 | Haissaguerre et al. | |
| 5,921,982 A | 7/1999 | Lesh et al. | |
| 5,925,045 A | 7/1999 | Reimels et al. | |
| 5,927,284 A | 7/1999 | Borst et al. | |
| 5,928,191 A | 7/1999 | Houser et al. | |
| 5,935,123 A | 8/1999 | Edwards et al. | |
| 5,941,876 A | 8/1999 | Nardella et al. | |
| 5,944,715 A | 8/1999 | Goble et al. | |
| 5,957,881 A | 9/1999 | Peters et al. | |
| 5,957,919 A | 9/1999 | Laufer | |
| 5,971,980 A | 10/1999 | Sherman | |
| 5,971,983 A | 10/1999 | Lesh | |
| 5,980,516 A | 11/1999 | Mulier et al. | |
| 5,989,248 A | 11/1999 | Tu et al. | |
| 5,993,412 A | 11/1999 | Deily et al. | |
| 6,004,316 A | 12/1999 | Laufer | |
| 6,004,319 A | 12/1999 | Goble et al. | |
| 6,010,476 A | 1/2000 | Saadat | |
| 6,010,500 A | 1/2000 | Sherman et al. | |
| 6,012,457 A | 1/2000 | Lesh | |
| 6,015,391 A | 1/2000 | Rishton et al. | |
| 6,024,733 A | 2/2000 | Eggers et al. | |
| 6,042,556 A | 3/2000 | Beach et al. | |
| 6,042,593 A | 3/2000 | Storz et al. | |
| 6,053,923 A | 4/2000 | Veca et al. | |
| 6,063,081 A | 5/2000 | Mulier | |
| 6,071,279 A | 6/2000 | Whayne et al. | |
| 6,074,386 A | 6/2000 | Goble et al. | |
| 6,088,894 A | 7/2000 | Oakley | |
| 6,096,037 A | 8/2000 | Mulier | |
| 6,117,101 A | 9/2000 | Diederich et al. | |
| 6,142,993 A | 11/2000 | Whayne et al. | |
| 6,142,994 A | 11/2000 | Swanson et al. | |
| 6,152,920 A | 11/2000 | Thompson et al. | |
| 6,152,941 A | 11/2000 | Himes et al. | |
| 6,161,543 A | 12/2000 | Cox et al. | |
| 6,165,174 A | 12/2000 | Jacobs et al. | |
| 6,193,715 B1 | 2/2001 | Wrublewski | |
| 6,197,025 B1 * | 3/2001 | Sullivan | 606/45 |
| 6,214,003 B1 * | 4/2001 | Morgan et al. | 606/50 |
| 6,217,528 B1 | 4/2001 | Koblish et al. | |
| 6,217,576 B1 | 4/2001 | Tu et al. | |
| 6,217,598 B1 | 4/2001 | Berman et al. | |
| 6,221,088 B1 | 4/2001 | Bays | |
| 6,224,592 B1 | 5/2001 | Eggers et al. | |
| 6,231,518 B1 | 5/2001 | Grabek et al. | |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier | |
| 6,245,061 B1 | 6/2001 | Panescu et al. | |

(56) References Cited

U.S. PATENT DOCUMENTS

| | | |
|---|---|---|
| 6,245,064 B1 | 6/2001 | Lesh et al. |
| 6,245,065 B1 | 6/2001 | Panescu et al. |
| 6,246,638 B1 | 6/2001 | Zook et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,292,689 B1 | 9/2001 | Wallace et al. |
| 6,293,943 B1 | 9/2001 | Panescu et al. |
| 6,293,957 B1 | 9/2001 | Peters et al. |
| 6,296,638 B1 | 10/2001 | Davison et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier et al. |
| 6,454,782 B1 | 9/2002 | Schwemberger |
| 6,461,357 B1 | 10/2002 | Sharkey et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,678 B2 | 12/2002 | Sherman |
| 6,488,680 B1 | 12/2002 | Francischelli |
| 6,494,892 B1 | 12/2002 | Ireland et al. |
| 6,502,575 B1 | 1/2003 | Jacobs et al. |
| 6,503,263 B2 | 1/2003 | Adams |
| 6,514,250 B1 | 2/2003 | Jahns et al. |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,558,385 B1 | 5/2003 | McClurken et al. |
| 6,565,560 B1 | 5/2003 | Goble et al. |
| 6,565,561 B1 | 5/2003 | Goble et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,716,215 B1 | 4/2004 | David et al. |
| 6,736,810 B2 | 5/2004 | Hoey |
| 6,752,816 B2 | 6/2004 | Culp et al. |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,780,180 B1 | 8/2004 | Goble et al. |
| 6,807,968 B2 | 10/2004 | Francischelli |
| 6,824,550 B1 | 11/2004 | Noriega et al. |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,923,803 B2 | 8/2005 | Goble |
| 6,936,046 B2 | 8/2005 | Hissong |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 6,979,332 B2 | 12/2005 | Adams |
| 7,052,494 B2 | 5/2006 | Goble et al. |
| 7,115,139 B2 | 10/2006 | McClurken et al. |
| 7,150,747 B1 | 12/2006 | McDonald et al. |
| 7,166,103 B2 | 1/2007 | Carmel et al. |
| 7,179,255 B2 | 2/2007 | Lettice et al. |
| 7,229,437 B2 | 6/2007 | Johnson et al. |
| 7,232,440 B2 | 6/2007 | Dumbauld et al. |
| 7,237,990 B2 | 7/2007 | Deng |
| 7,247,155 B2 | 7/2007 | Hoey et al. |
| 7,247,161 B2 | 7/2007 | Johnston et al. |
| 7,261,711 B2 | 8/2007 | Mulier et al. |
| 7,276,074 B2 | 10/2007 | Adams et al. |
| 7,278,994 B2 | 10/2007 | Goble |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,416,539 B2 | 8/2008 | Johnston et al. |
| 7,442,191 B2 | 10/2008 | Hovda et al. |
| 7,537,595 B2 | 5/2009 | McClurken |
| 7,604,635 B2 | 10/2009 | McClurken et al. |
| 7,608,072 B2 | 10/2009 | Swanson |
| 7,645,277 B2 | 1/2010 | McClurken et al. |
| 7,651,494 B2 | 1/2010 | McClurken et al. |
| 7,674,263 B2 | 3/2010 | Ryan |
| 7,691,050 B2 | 4/2010 | Gellman |
| 7,736,361 B2 | 6/2010 | Palanker |
| 7,749,608 B2 | 7/2010 | Laude et al. |
| 7,785,337 B2 | 8/2010 | Adams et al. |
| 7,811,282 B2 | 10/2010 | McClurken |
| 7,815,634 B2 | 10/2010 | McClurken et al. |
| 7,854,736 B2 | 12/2010 | Ryan |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,012,153 B2 | 9/2011 | Woloszko et al. |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | McClurken et al. |
| 8,105,323 B2 | 1/2012 | Buysse et al. |
| 8,109,956 B2 | 2/2012 | Shadeck |
| 8,172,828 B2 | 5/2012 | Chang et al. |
| 8,177,783 B2 | 5/2012 | Davison et al. |
| 8,202,288 B2 | 6/2012 | Adams et al. |
| 8,216,233 B2 | 7/2012 | McClurken |
| 8,317,786 B2 | 11/2012 | Dahla et al. |
| 8,323,276 B2 | 12/2012 | Palanker et al. |
| 8,348,946 B2 | 1/2013 | McClurken |
| 8,361,068 B2 | 1/2013 | McClurken |
| 8,377,086 B2 | 2/2013 | Flynn et al. |
| 8,388,642 B2 | 3/2013 | Muni et al. |
| 8,414,572 B2 | 4/2013 | Davison et al. |
| 8,568,419 B2 | 10/2013 | deWekker |
| 2001/0047183 A1 | 11/2001 | Privitera et al. |
| 2002/0038129 A1 | 3/2002 | Peters et al. |
| 2002/0049483 A1 | 4/2002 | Knowlton |
| 2002/0062131 A1 | 5/2002 | Gallo, Sr. |
| 2002/0082643 A1 | 6/2002 | Milla et al. |

(56) References Cited

U.S. PATENT DOCUMENTS

| | | |
|---|---|---|
| 2002/0165549 A1 | 11/2002 | Owusu-Akyaw et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0097129 A1 | 5/2003 | Davison et al. |
| 2003/0144656 A1 | 7/2003 | Ocel |
| 2003/0165794 A1 | 9/2003 | Matoba |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0010258 A1 | 1/2004 | Carusillo et al. |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0167427 A1 | 8/2004 | Quick et al. |
| 2004/0186465 A1 | 9/2004 | Francischelli |
| 2004/0215183 A1 | 10/2004 | Hoey et al. |
| 2004/0220560 A1 | 11/2004 | Briscoe |
| 2004/0236322 A1 | 11/2004 | Mulier |
| 2004/0243163 A1 | 12/2004 | Casiano et al. |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux et al. |
| 2005/0209564 A1 | 9/2005 | Bonner |
| 2005/0222566 A1 | 10/2005 | Nakahira |
| 2005/0267454 A1 | 12/2005 | Hissong |
| 2005/0277970 A1 | 12/2005 | Norman et al. |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0259055 A1 | 11/2006 | Thorne et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Sr. et al. |
| 2007/0179495 A1* | 8/2007 | Mitchell et al. ............ 606/41 |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0207028 A1 | 8/2008 | Schutz |
| 2008/0262489 A1 | 10/2008 | Steinke |
| 2009/0118729 A1 | 5/2009 | Auth et al. |
| 2009/0264879 A1 | 10/2009 | McClurken et al. |
| 2009/0270896 A1 | 10/2009 | Sullivan et al. |
| 2009/0306655 A1 | 12/2009 | Stangeness |
| 2010/0087812 A1 | 4/2010 | Davison et al. |
| 2010/0100095 A1 | 4/2010 | McClurken et al. |
| 2010/0160906 A1 | 6/2010 | Jarrard |
| 2010/0241178 A1 | 9/2010 | Tilson et al. |
| 2010/0298763 A1 | 11/2010 | Adams et al. |
| 2010/0317998 A1 | 12/2010 | Hibner et al. |
| 2011/0009856 A1 | 1/2011 | Jorgensen et al. |
| 2011/0017801 A1 | 1/2011 | Zemlok et al. |
| 2011/0028965 A1 | 2/2011 | McClurken |
| 2011/0066142 A1 | 3/2011 | Tal et al. |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0301578 A1 | 12/2011 | Muniz-Medina et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0101496 A1 | 4/2012 | McClurken et al. |
| 2012/0109130 A1 | 5/2012 | Casey et al. |
| 2012/0116397 A1 | 5/2012 | Rencher et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0172877 A1 | 7/2012 | Ryan et al. |
| 2012/0179158 A1 | 7/2012 | Stierman |
| 2012/0184983 A1 | 7/2012 | Chang et al. |
| 2012/0191084 A1 | 7/2012 | Davison et al. |
| 2012/0191117 A1 | 7/2012 | Palmer et al. |
| 2012/0215245 A1 | 8/2012 | Palmer et al. |
| 2012/0221035 A1 | 8/2012 | Harvey |
| 2012/0253343 A1 | 10/2012 | McClurken et al. |
| 2013/0004595 A1 | 1/2013 | Bhatia |
| 2013/0053830 A1 | 2/2013 | Edwards et al. |
| 2013/0085498 A1 | 4/2013 | Matusaitis et al. |
| 2013/0345704 A1 | 12/2013 | Palmer et al. |
| 2014/0005700 A1 | 1/2014 | Casey et al. |
| 2014/0100567 A1 | 4/2014 | Edwards et al. |
| 2014/0155888 A1 | 6/2014 | Edwards et al. |
| 2014/0155889 A1 | 6/2014 | Edwards et al. |
| 2014/0155923 A1 | 6/2014 | Edwards et al. |
| 2014/0277036 A1 | 9/2014 | Flynn et al. |

FOREIGN PATENT DOCUMENTS

| | | |
|---|---|---|
| EP | 2133028 | 12/2009 |
| EP | 1853187 | 10/2011 |
| GB | 2470607 | 12/2010 |
| WO | 96/37156 | 11/1996 |
| WO | 97/23169 | 7/1997 |
| WO | WO/98/34550 | 8/1998 |
| WO | 98/38932 | 9/1998 |
| WO | WO/03/079911 | 10/2003 |
| WO | 2011037664 | 3/2011 |
| WO | 2012102838 | 8/2012 |
| WO | 2014/084983 | 6/2014 |
| WO | 2014/133663 | 9/2014 |

OTHER PUBLICATIONS

Berger et al., Histopathological Changes After Coblation Inferior Turbinate Reduction, Arch Otolaryngol Head Neck Surg. 2008;134(8):819-823.

Arthrocare PROcise EZ View Sinus Wand with integrated ablation, suction, and bipolar hemostasis (1 page) admitted prior art document.

U.S. Appl. No. 61/666,131, filed Jun. 9, 2012, Matusaitis, et al.

U.S. Appl. No. 61/697,082, filed Sep. 5, 2012, Matusaitis, et al.

U.S. Appl. No. 61/731,919, filed Nov. 30, 2012, Edwards, et al.

U.S. Appl. No. 61/769,480, filed Feb. 26, 2013, Edwards, et al.

Cosman et al., Radiofrequency lesion generation and its effect on tissue impedance, Applied Neurophysiology (1988) 51: 230-242.

Thanos et al., Image-Guided Radiofrequency Ablation of a Pancreatic Tumor with a New Triple Spiral-Shaped Electrode, Cardiovasc Intervent Radiol (2010) 33:215-218.

McGahan JP, Brock JM, Tesluk H et al., Hepatic ablation with use of radio-frequency electrocautery in the animal model. J Vasc Interv Radiol, May 1992; 3:291-297.

Siefert et al. Radiofrequency Maze Ablation for Atrial Fibrillation, Circulation 90(4): I-594.

Dr. Krakovitz, "Olympus, PK DIEGO Tonsil and Adenoid Application Guide," Gyrus ENT, LLC, 2011.

* cited by examiner

DEBRIDEMENT DEVICE AND METHOD

CROSS-REFERENCE TO RELATED APPLICATIONS

This application is related to and claims the benefit of U.S. provisional application 61/658,724, filed Jun. 12, 2012 and of U.S. Provisional Application 61/704,904, filed Sep. 24, 2012, the entire disclosures of which are hereby incorporated by reference in their respective entireties.

BACKGROUND

The present invention is generally directed to devices, systems and methods for cutting and sealing tissue such as bone and soft tissue. The present invention may be particularly suitable for sinus applications and nasopharyngeal/laryngeal procedures and may combine or provide Transcollation® technology with a microdebrider device.

Devices, systems and methods according to the present disclosure may be suitable for a variety of procedures including ear, nose and throat (ENT) procedures, head and neck procedures, otology procedures, including otoneurologic procedures. The present disclosure may be suitable for a varient of other surgical procedures including mastoidectomies and mastoidotomies; nasopharyngeal and laryngeal procedures such as tonsillectomies, trachael procedures, adenoidectomies, laryngeal lesion removal, and polypectomies; for sinus procedures such as polypectomies, septoplasties, removals of septal spurs, anstrostomies, frontal sinus trephination and irrigation, frontal sinus opening, endoscopic DCR, correction of deviated septums and trans-sphenoidal procedures; rhinoplasty and removal of fatty tissue in the maxillary and mandibular regions of the face.

Sinus surgery is challenging due to its location to sensitive organs such as the eyes and brain, the relatively small size of the anatomy of interest to the surgeon, and the complexity of the typical procedures. Examples of debriders with mechanical cutting components are described in U.S. Pat. Nos. 5,685,838; 5,957,881 and 6,293,957. These devices are particularly successful for powered tissue cutting and removal during sinus surgery, but do not include any mechanism for sealing tissue to reduce the amount of bleeding from the procedure. Sealing tissue is especially desirable during sinus surgery which tends to be a complex and precision oriented practice.

Electrosurgical technology was introduced in the 1920's. In the late 1960's, isolated generator technology was introduced. In the late 1980's, the effect of RF lesion generation was well known. See e.g., Cosman et al., *Radiofrequency lesion generation and its effect on tissue impedance*, Applied Neurophysiology (1988) 51: 230-242. Radiofrequency ablation is successfully used in the treatment of unresectable solid tumors in the liver, lung, breast, kidney, adrenal glands, bone, and brain tissue. See e.g., Thanos et al., *Image-Guided Radiofrequency Ablation of a Pancreatic Tumor with a New Triple Spiral-Shaped Electrode*, Cardiovasc. Intervent. Radiol. (2010) 33:215-218.

The use of RF energy to ablate tumors or other tissue is known. See e.g., McGahan J P, Brock J M, Tesluk H et al., *Hepatic ablation with use of radio-frequency electrocautery in the animal model*. J Vasc Interv Radiol 1992; 3:291-297. Products capable of aggressive ablation can sometimes leave undesirable charring on tissue or stick to the tissue during a surgical procedure. Medical devices that combine mechanical cutting and an electrical component for cutting, ablating or coagulating tissue are described, for example, in U.S. Pat. Nos. 4,651,734 and 5,364,395.

Commercial medical devices that include monopolar ablation systems include the Invatec MIRAS RC, MIRAS TX and MIRAS LC systems previously available from Invatec of Italy. These systems included a probe, a grounding pad on the patient and a generator that provides energy in the range of 450 to 500 kHz. Other examples of RF bipolar ablation components for medical devices are disclosed in U.S. Pat. Nos. 5,366,446 and 5,697,536.

Medical devices are also used to ablate heart tissue with RF energy. See, e.g., Siefert et al. *Radiofrequency Maze Ablation for Atrial Fibrillation*, Circulation 90(4): I-594. Some patents describing RF ablation of heart tissue include U.S. Pat. Nos. 5,897,553, 6,063,081 and 6,165,174. Devices for RF ablation of cardiac tissue are typically much less aggressive than RF used to cut tissue as in many procedures on cardiac tissue, a surgeon only seeks to kill tissue instead of cutting or removing the tissue. Cardiac ablation of this type seeks to preserve the structural integrity of the cardiac tissue, but destroy the tissue's ability to transfer aberrant electrical signals that can disrupt the normal function of the heart.

Transcollation® technology, for example, the sealing energy supplied by the Aquamantys® System (available from Medtronic Advanced Energy of Portsmouth, N.H.) is a patented technology which stops bleeding and reduces blood loss during and after surgery and is a combination of radiofrequency (RF) energy and saline that provides hemostatic sealing of soft tissue and bone and may lower transfusion rates and reduce the need for other blood management products during or after surgery. Transcollation® technology integrates RF energy and saline to deliver controlled thermal energy to tissue. Coupling of saline and RF energy allows a device temperature to stay in a range which produces a tissue effect without the associated charring found in other ablation methods.

Other ablation devices include both mechanical cutting as well as ablation energy. For example, the PK diego® powered dissector is commercially available from Gyms ENT of Bartlett, Tenn. This device utilizes two mechanical cutting blade components that are moveable relative to each other, one of which acts as an electrode in a bipolar ablation system. The distal end portion of the device includes six layers to accomplish mechanical cutting and electrical coagulation. The dual use of one of the components as both a mechanical, oscillating cutting element and a portion of the bipolar system of the device is problematic for several reasons. First, the arrangement exposes the sharp mechanical cutting component to tissue just when hemostasis is sought. In addition, the electrode arrangement does not provide for optimal application of energy for hemostasis since the energy is applied essentially at a perimeter or outer edge of a cut tissue area rather than being applied to a central location of the cut tissue. The arrangement of the device also requires more layers than necessary in the construction of a device with both sharp cutters and RF ablation features. The overabundance of layers can make it difficult to design a small or optimally-sized distal end. Generally speaking, the larger the distal end, the more difficult it is for the surgeon to visualize the working surfaces of the device. The use of six layers at the distal end of the system also interferes with close intimate contact between the tissue and the electrodes. Some examples of cutting devices are described in U.S. Pat. Nos. 7,854,736 and 7,674,263.

The Medtronic Straightshot® M4 Microdebrider uses sharp cutters to cut tissue, and suction to withdraw tissue. While tissue debridement with the Medtronic microdebrider system is a simple and safe technique, some bleeding may occur. The Medtronic microdebrider does not include a feature dedicated to promoting hemostasis or bleeding management. Thus, nasal packing is often used.

BRIEF DESCRIPTION OF THE DRAWINGS

In the drawings, where like numerals refer to like components throughout several views.

DETAILED DESCRIPTION

Figure 1:
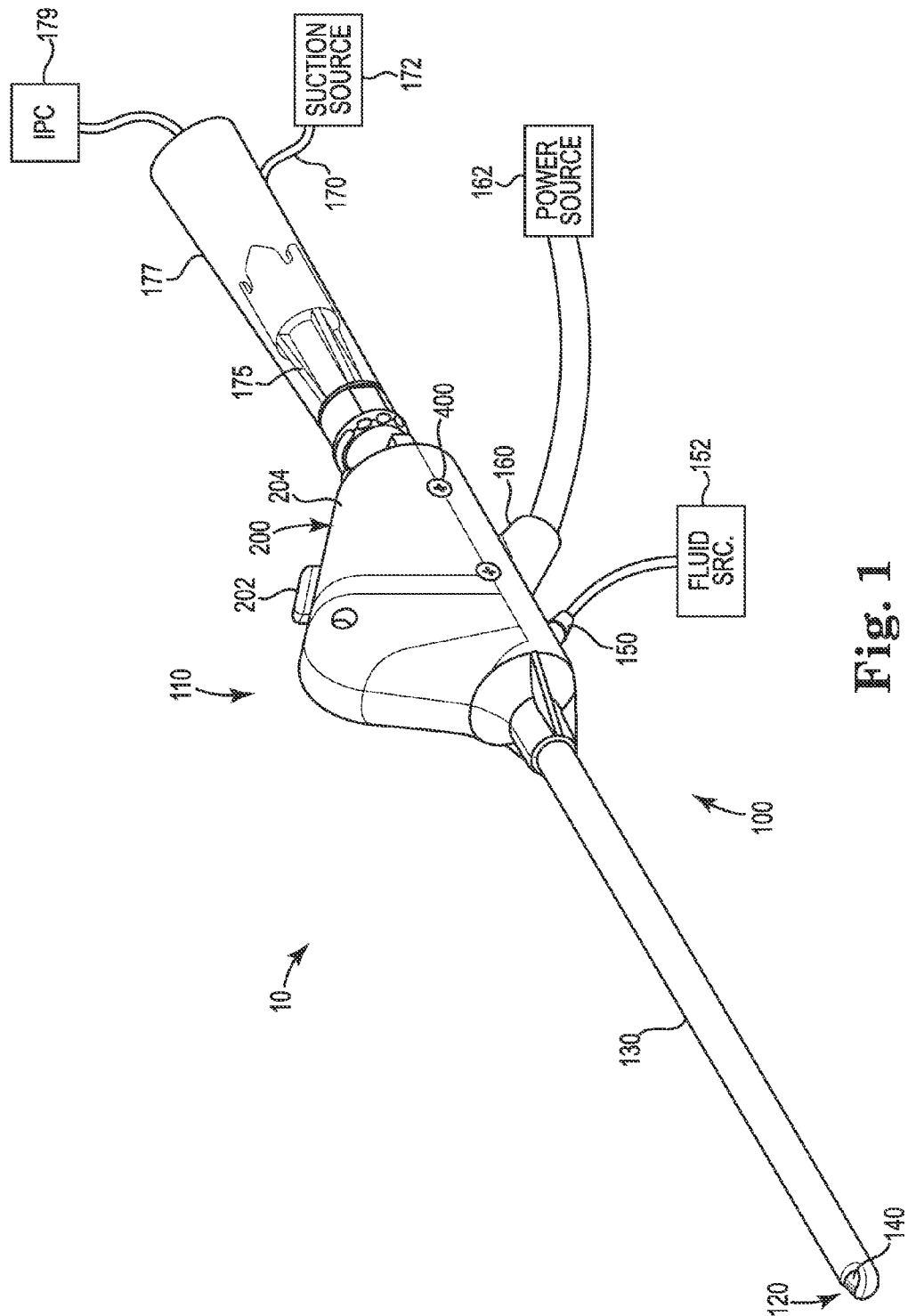
FIG. 1 is a perspective view of a system according to one aspect of the present invention.

FIG. 1 illustrates a system 10 according to an aspect of the present invention. The system 10 includes a device 100 having a distal end region indicated generally at 120 and a proximal end region indicated generally at 110. The device includes an outer shaft 130 and an inner shaft 140 coaxially maintained within the outer shaft 130. A portion of the inner shaft 140 is shown in FIG. 1 at distal end region 120. Proximal end region 110 includes a button activation cell 200 comprising a housing 204 and a button 202, the proximal end region further comprising a hub 175 coupled to inner shaft 140. The hub is configured to couple to a handle or handpiece 177 which can be manipulated by a user (e.g., a surgeon). The handpiece 177, in turn may be coupled to an integrated power console or IPC 179 for driving the device 100 and specifically for controlling rotation of inner shaft 140. The IPC 179 may also include a fluid source (not shown) and may provide fluid delivery to device 100.

Proximal end region 110 also includes a fluid source connector 150, a power source connector 160 and a suction source connector 170 for connection to a fluid source 152, a power source, 162 and/or a suction source of system 10. One fluid useful with the present disclosure is saline, however, other fluids are contemplated. Power source 162 may be a generator and optionally may be designed for use with bipolar energy or a bipolar energy supply. For example, the Transcollation® sealing energy supplied by the Aquamantys® System (available from Medtronic Advanced Energy of Portsmouth, N.H.) may be used. Both the fluid source 152 and suction source 172 are optional components of system 10. However, use of fluid in conjunction with energy delivery aids in providing optimal tissue effect as will be further explained, thus embodiments of the present invention include specific arrangement of the device 100 for coupling of energy with a fluid. In use, a fluid (e.g., saline) may be emitted from an opening at the distal end region of the device 100. Tissue fragments and fluids can be removed from a surgical site through an opening (not shown in FIG. 1) in the distal end region via the suction source 172, as will be further explained below.

Figure 2:
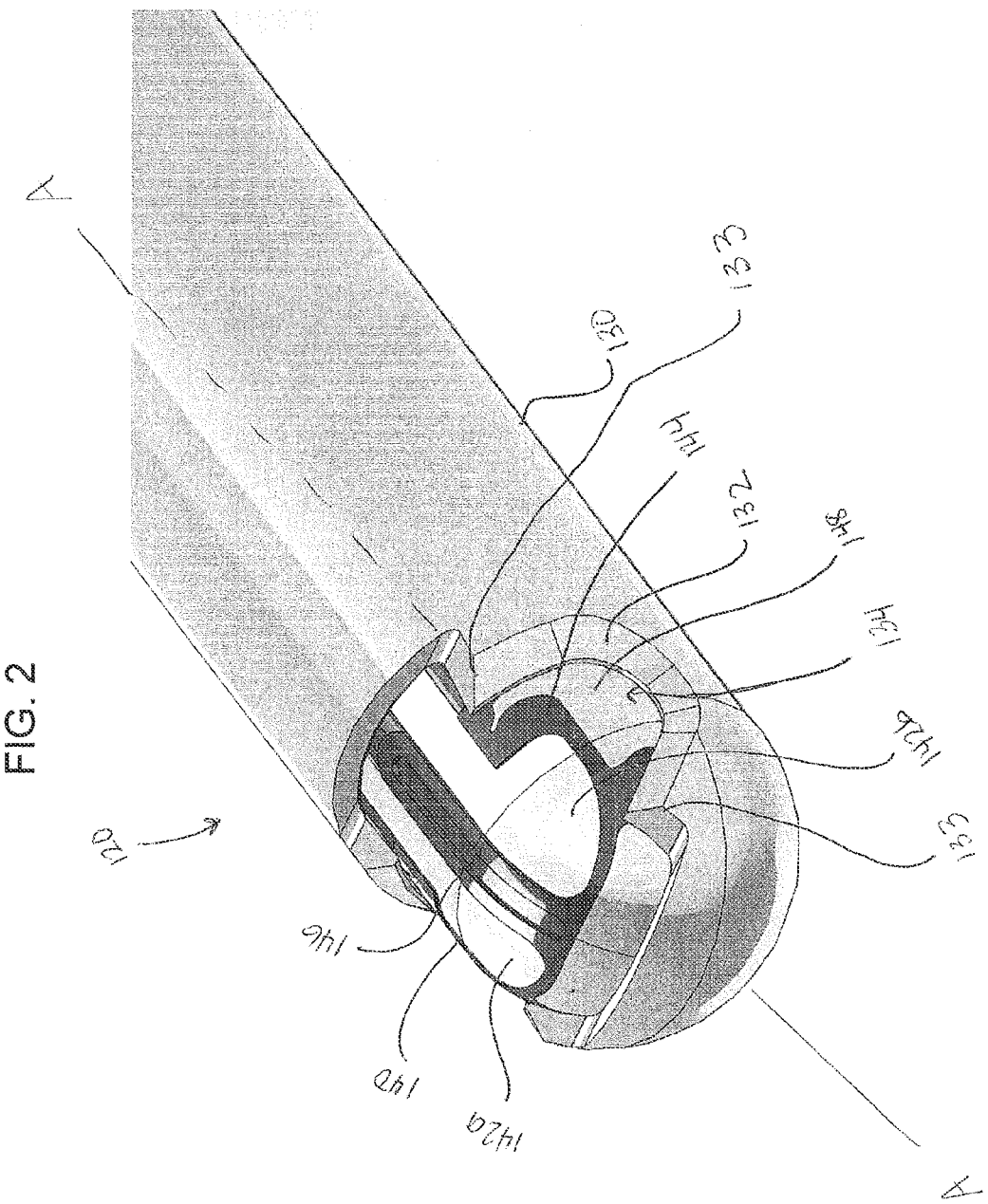
FIG. 2 is a perspective view of a distal end region of a device with an inner shaft in a position according to one aspect of the present invention.
Figure 3:
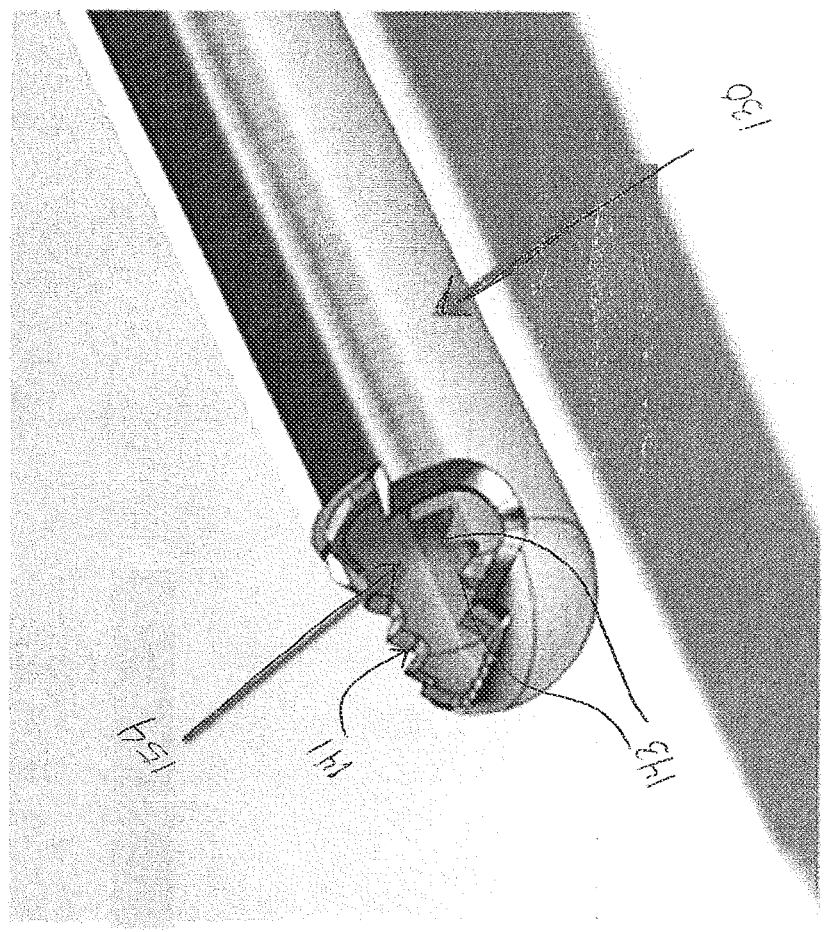
FIG. 3 is a perspective view of the distal end region of a device with an inner shaft in an alternative position according to one aspect of the present invention.

FIG. 2 shows an enlarged perspective view of distal end portion 120 of device 100. The outer shaft 130 includes a window or opening 134 at a distal end 135 of the outer shaft 135. Window 134 is defined by an outer shaft cutting edge or cutter 132, which comprises cutting teeth 133. The outer shaft 130 may be rigid or malleable or combinations thereof and may be made of a variety of metals and/or polymers or combinations thereof, for example may be made of stainless steel. A distal portion 148 of the inner shaft 140 can be seen through the window or opening 134 of outer shaft 130. In FIG. 1, inner shaft 140 is depicted in a position such that an inner shaft cutting edge or cutter 141 (FIG. 3), comprising cutting teeth 143 is facing an inner wall (not shown) of outer shaft 130. Cutter 141 defines an inner shaft window or opening 154 (FIG. 3). Outer and inner shaft cutters 132 and 141 may move relative to one another in oscillation or rotation (or both) in order to mechanically cut tissue. For example, outer shaft cutter 132 may remain stationary relative to the hub 175 and button assembly 200 while the inner shaft cutter 141 may rotate about a longitudinal axis A of the device, thereby cutting tissue.

Rotation of inner shaft 140 may be achieved via manipulation of hub 175 (FIG. 1). that can orient the inner shaft 140 relative to the outer shaft 130 and may additionally allow for locking of the inner shaft relative to the outer shaft in a desired position, i.e., inner shaft may be locked in position when cutter 141 is facing down and electrode assembly 142 is facing up. As described above, hub 175 may be connected to a handle or handpiece 177 which may be controlled by an IPC 179. Alternatively, the hub 175 and/or handle portions may be manipulated manually. Inner shaft 140 may be selectively rotated to expose an electrode assembly 142 comprising electrodes 142a, 142b, through opening 134 of outer shaft 130, as shown in FIG. 2. Electrodes 142a, 142b may comprise electrode traces and the electrode traces may extend from the distal portion 148 of the inner shaft to a proximal end 151 (FIG. 10) of the inner shaft 140. As depicted in FIG. 2, inner shaft 140 is positioned such that the inner shaft cutter 141 is facing the interior (not shown) of outer shaft 130 and may be said to be in a downward facing direction and comprise a downward position. In the downward position, tissue is shielded from the inner shaft cutter 141 during hemostasis (via energy delivery through electrodes 142a, 142b), thereby delivering energy to tissue with no attendant risk that the cutting teeth 143 of the inner shaft 140 will diminish the efforts to achieve hemostasis. Device 100 may thus comprise two modes: a cutting or debridement mode and a sealing or hemostasis mode and the two modes may be mutually exclusive, i.e. hemostasis is achieved via energy delivery to tissue while cutters 132, 141 are not active or cutting. As described below, energy may be advantageously delivered simultaneously with a fluid such as saline to achieve an optimal tissue effect by delivering controlled thermal energy to tissue.

Figure 7:
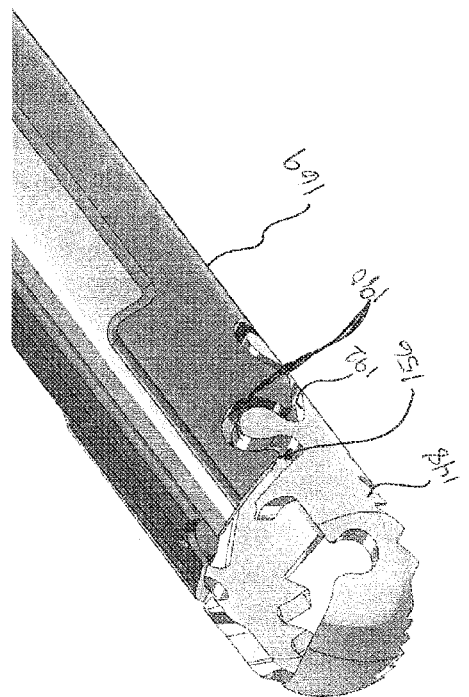
FIG. 7 is a perspective view of the distal end region of FIG. 6 with components removed.

As depicted in FIG. 3, when the inner shaft 140 is oriented such that the cutter 141 is in the downward position, rotating inner shaft 140 approximately 180 degrees relative to the outer shaft 130 will expose inner shaft cutter 141 and inner shaft opening 154 through the outer shaft opening 134. When the inner shaft cutter 141 is positioned as shown in FIG. 3, the inner shaft cutter 141 may be said to be in an upward position. The inner shaft opening 154 is fluidly connected to an inner shaft lumen 156, a portion of which can be seen in FIG. 7. Lumen 156 extends from the inner shaft distal portion 148 to the proximal end 151 (FIG. 10) of inner shaft 140 and may be fluidly connected with the suction source 172. With this configuration, tissue cut via inner and outer shaft cutters 141, 132 may be aspirated into the inner shaft lumen 156 through the inner shaft opening 154 upon application of suction source 172, thereby removing tissue from a target site.

Figure 4:
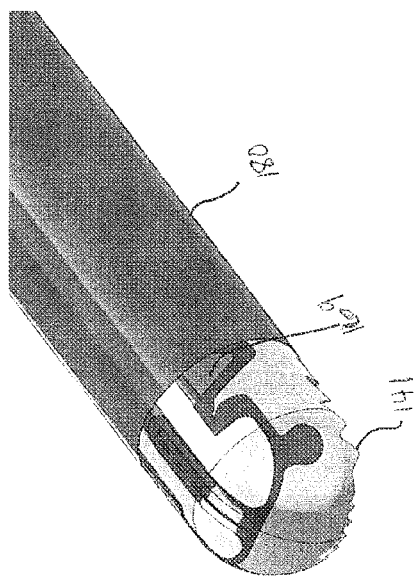
FIG. 4 is a perspective view the distal end region of FIG. 2 with an outer shaft removed to show portions of an inner shaft and insulation liner.
Figure 5:
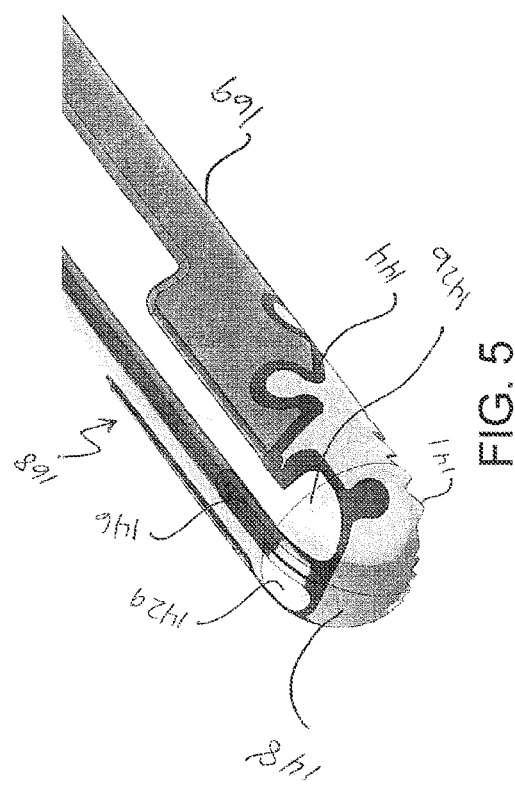
FIG. 5 is a perspective view of the distal end region of FIG. 4 with the insulation liner removed to show additional portions of the inner shaft and electrode traces.

With reference between FIGS. 4 and 5, the inner shaft 140 comprises a proximal assembly 168 including a proximal assembly shaft component 169 (more clearly seen in FIG. 5) and electrodes 142a and 142b. Inner shaft 140 also includes a joining assembly 144, which may be a non-conductive component and more specifically may comprise a liquid crystal polymer (LCP) overmold assembly. The joining assembly 144 may effectively join or connect the distal portion 148 of inner shaft 140 with the proximal assembly shaft component 169 (most clearly depicted in FIG. 5). Joining assembly 144 includes an extension portion 146 which aids in minimizing arc tracking from the electrodes 142a and 142b as will be further elucidated in the following discussion.

Electrodes or electrode traces 142a and 142b comprise bipolar electrodes and may comprise wet or dry electrodes. Electrodes 142a and 142b may be used to deliver any suitable energy for purposes of coagulation, hemostasis or sealing of tissue. Electrodes 142a and 142b are particularly useful with fluid such as saline provided by fluid source 152 (FIG. 1) which may be emitted near the outer shaft opening 134. Outer shaft opening 134 is fluidly connected to an outer shaft lumen 136, shown in phantom in FIG. 7. Lumen 136 extends from outer shaft opening 134 to the proximal end region 110 of device 100 and may be fluidly connected to the fluid source 152 (FIG. 1). Thus, fluid can be delivered to the opening 134 of outer shaft 130 and interacts with electrode traces 142a, 142b, as will be further described with reference to FIG. 1. In this manner, electrode traces 142a and 142b can advantageously provide Transcollation® sealing of tissue when used with the Transcollation® sealing energy supplied by the Aquamantys System, available from the Advanced Energy Division of Medtronic, Inc. With respect to "wet" RF coagulation technology, the technology for sealing tissue described in U.S. Pat. Nos. 6,558,385; 6,702,810; 6,953,461; 7,115,139; 7,311,708; 7,537,595; 7,645,277; 7,811,282; 7,998,140; 8,048,070; 8,083,736; and 8,361,068 (the entire contents of each of which is incorporated by reference) describe bipolar coagulation systems believed suitable for use in the present invention. Other systems for providing a source of energy are also contemplated.

Both FIGS. 4 and 5 depict the distal end region 120 of device 100, with outer shaft 130 removed. FIG. 4 shows a portion of the inner shaft 140 coaxially maintained in an insulation liner or sheath 180. The liner 180 may extend from a location proximal the inner shaft cutter 141 and cutting teeth 143, along inner shaft 140, to the proximal end 151 of inner shaft 140. Liner 180 provides insulation between the inner and outer shafts 130, 140, thus providing electrical isolation of the electrodes 142a and 142b from outer shaft 130 as well as from one another while only adding a single, very thin layer to the overall device 100. Liner 180 may be made of any suitable material, for example, fluorinated ethylene propylene (FEP), polytetrafluoroethylene (PTFE), or any other material suitable as a non-conductive or electrically insulative material. Regardless, liner 180 is constructed so as to be negligible in its contribution to the overall diameter of the device 100 and particularly the distal end region 120 of the device 100.

Figure 6:
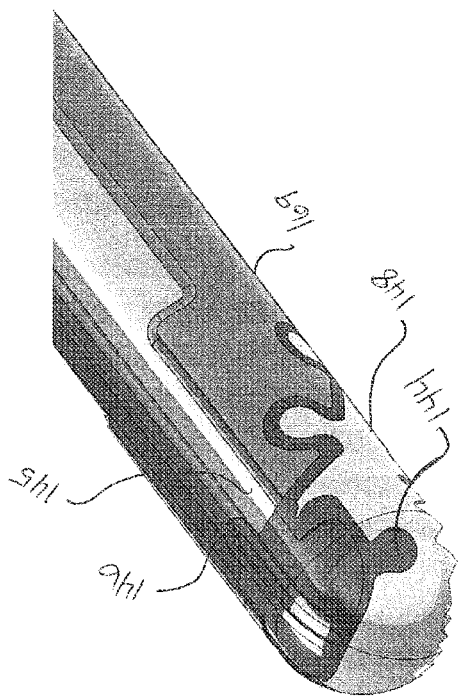
FIG. 6 is a perspective view of the distal end region of FIG. 5 with the electrode traces removed.

FIG. 5 shows the distal end region 120 of device 100 with both the outer shaft 130 and the insulation liner 180 removed, thus exposing only portions of inner shaft 140. As described above, inner shaft 140 includes a distal portion 148, which includes cutter 141, and an inner shaft proximal assembly 168 including proximal assembly shaft component 169. The individual distal portion 148 and shaft component 169 can be seen more clearly in FIG. 7 in which the joining assembly 144 and electrodes 142a, 142b are removed. The proximal assembly shaft component 169 may comprise a variety of suitable materials and for example, may comprise a liquid crystal polymer (LCP) extruded shaft component that is configured to support the placement of metallized conductors (e.g., electrodes 142a, 142b) and may support overmolding (e.g. of joining assembly 144) and/or a plating process, such as described below. Proximal assembly shaft component 169 may undergo a laser etching process to form the depressed areas 145 suitable for electrode placement or plating. Other methods of forming the depressed areas 145 are also contemplated. FIG. 6 shows inner shaft 140 with the electrodes or electrode traces 142a, 142b removed from the proximal portion 168 and joining assembly 144. Electrodes 142a and 142b may be formed on the proximal assembly shaft component 169 and on a portion of joining assembly 144 in a plating process for forming electrode traces. The portion over which the electrode traces may be applied includes depressed areas 145 (FIG. 6), which may be laser etched areas. One process of electrode plating may include first applying copper sufficient to conduct the desired power and then adding nickel and gold layers to the laser etched area 145. Other metals and combinations of metals are also contemplated, for example, silver may be used or any other metal or combination of metals effective in providing a cross section which meets power requirements for the energy delivery. Regardless, the plating process and overall electrode 142a, 142b thickness or depth is configured such that the electrodes 142a, 142b do not negatively impact the diameter of the device 100. As but one example, the electrode plating process may result in a dimensional change to the overall diameter as little as 0.0015".

FIG. 5 also more fully depicts joining assembly 144 which joins the distal portion 148 with the inner shaft proximal assembly 168 of the inner shaft 140. As seen in FIG. 5, portions of distal portion 148 and proximal assembly shaft component 169 may be configured in a "puzzle piece" arrangement as is indicated at joining assembly 144 which follows the lines of the puzzle piece. Each of the distal portion 148 and proximal assembly shaft component 169 include a mating edge 192, 190, respectively. This configuration distributes forces acting on the inner shaft 140 when the device 100 is in a cutting mode to aid in a secure coupling of the distal portion 148 and shaft component 169. The joining assembly extension portion 146 is located between electrodes 146a and 146*b*. This extension portion 146 provides adequate space between the electrodes 146*a*, 146*b* to mitigate arc tracking between the two and to improve the tissue depth effect.

Returning to FIG. 1, when fluid from fluid source 152 is provided through lumen 136 of the outer shaft 130, the fluid may travel between the outside diameter of the inner shaft 140 and the inside diameter of the outer shaft 130 to the distal end 120 of device 100. Fluid travels distally down the lumen 136 of outer shaft 130 and may "pool" in an area shown in FIG. 1 as essentially defined by the opening 134 of outer shaft 130. Likewise, electrodes 142*a* and 142*b* may be located slightly below the surface of the joining assembly 144 and/or the inner shaft proximal portion 168 (FIGS. 4, 5), creating another area for fluid pooling. This depressed electrode 142*a*, 142*b* surface can also prevent wear of the electrodes 142*a*, 142*b*. Pooling of fluid at the electrodes 142*a*, 142*b* allows for effective interaction between the fluid and the electrodes which in turn can provide effective and advantageous sealing of tissue, and in particular may provide effective Transcollation® sealing of tissue.

With continued reference to FIG. 1, electrodes 142*a* and 142*b* are situated in an area generally centrally located with respect to the outer shaft opening 134 when inner shaft cutter 141 is in a downward position. This generally central location of the electrodes 142*a*, 142*b* allows for energy delivery at an optimal point of debridement. In other words, after inner shaft cutter 141 and outer shaft cutter 132 are rotated or oscillated relative to one another to cut tissue, rotating inner shaft cutter 141 to the downward position to expose electrodes 142*a*, 142*b* and deliver energy through the electrodes 142*a*, 142*b* may allow for hemostasis in an area generally central to where debridement or cutting of tissue had taken place. The generally centered electrodes 142*a*, 142*b* allow for energy to essentially travel or radiate outwardly from the electrodes 142*a*, 142*b* to coagulate the approximately the entire area of tissue previously cut. In other words, energy, and particularly RF energy may be provided at the center or near center of a portion of tissue previously cut or debrided.

Figure 8:
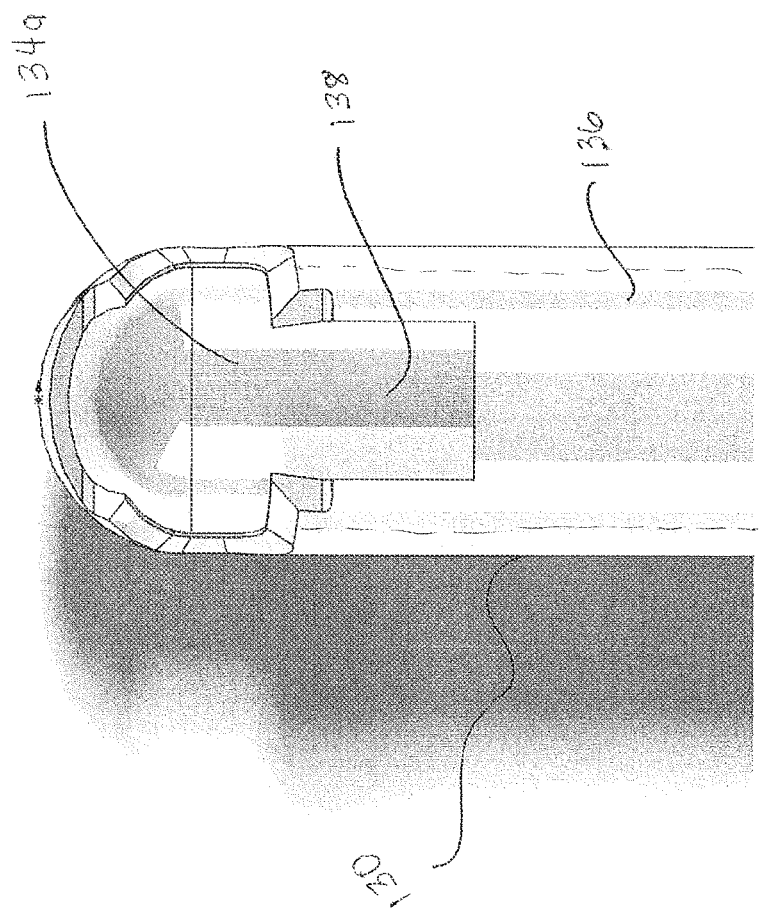
FIG. 8 is a perspective view of another embodiment of a distal end portion of an outer shaft of a device according the present invention.
Figure 9:
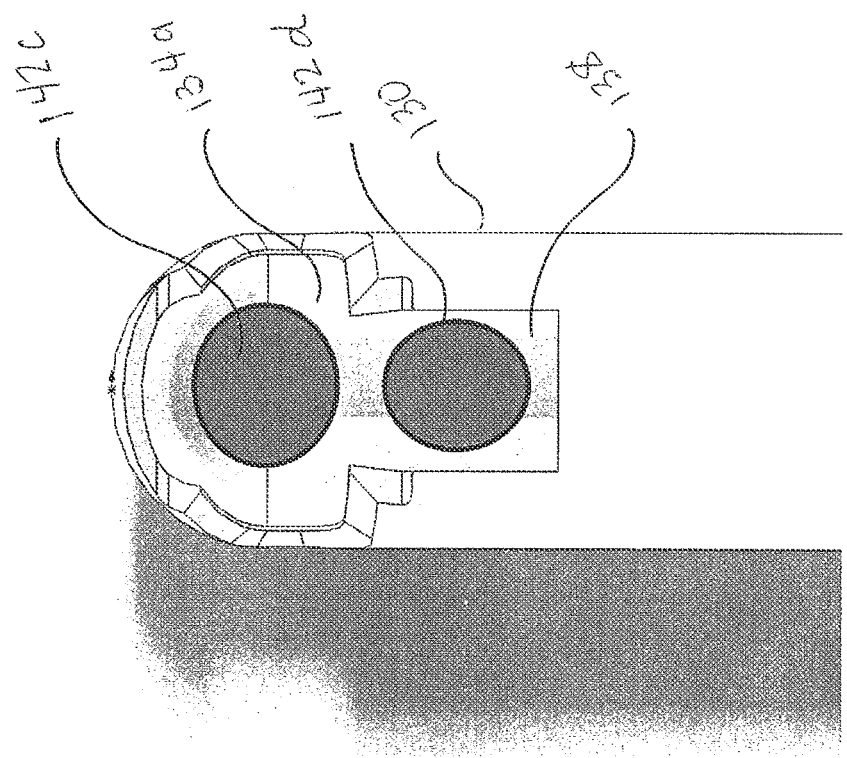
FIG. 9 is a perspective view the outer shaft of FIG. 8 showing a partial electrode configuration according to an aspect of the present invention.

FIGS. 8 and 9 depict an alternative outer shaft 130 and inner shaft 140 whereby an outer shaft window or opening 134*a* is essentially enlarged as compared to outer shaft window 134 (FIG. 2) via a proximal window portion 138. This enlarged opening 134*a* may afford an inner shaft 140 having significantly larger electrodes 142*c*, 142*d*, such as depicted in FIG. 9. Electrodes 142*c*, 142*d* may be otherwise constructed similar to electrodes 142*a* and 142*b* (e.g., FIG. 2) and the remaining portions of inner shaft 140 may be constructed as described above.

Figure 10:
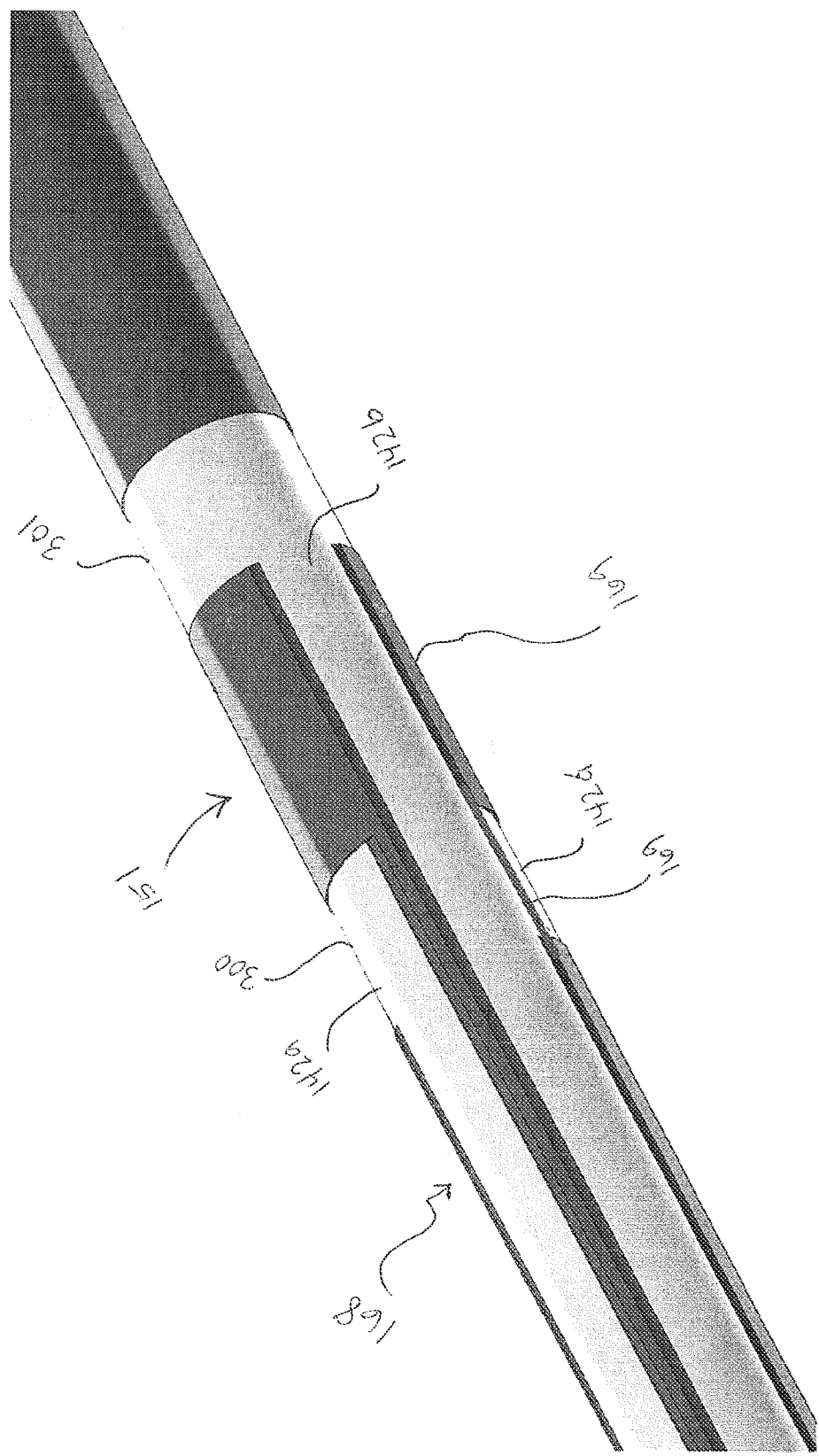
FIG. 10 is a perspective view of a proximal end of an inner shaft according to an aspect of the present invention.
Figure 14:
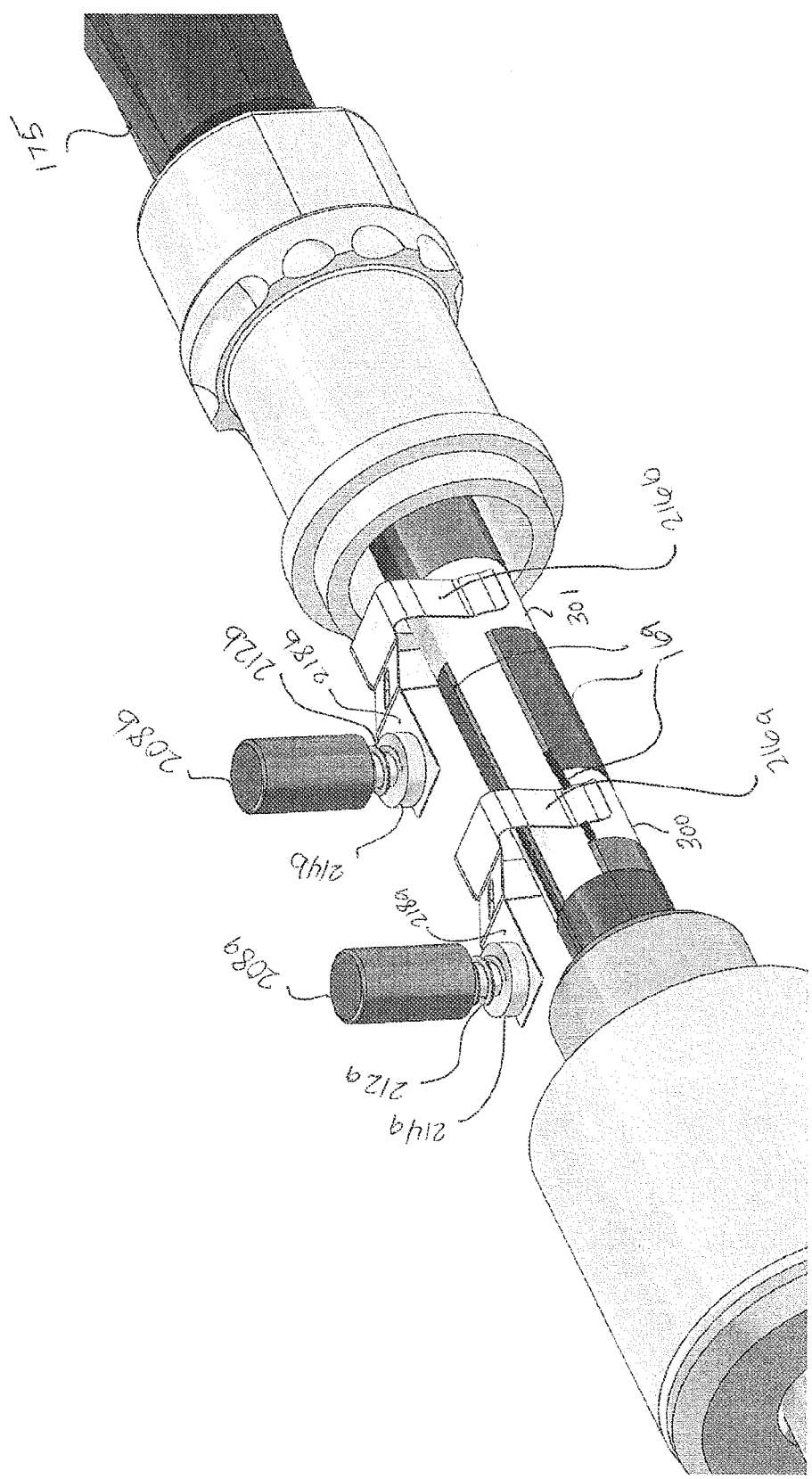
FIG. 14 is a perspective view of the assembly of FIG. 13 with portions removed according to an aspect of the present invention.

FIG. 10 depicts a section of proximal assembly 168 of inner shaft 140 which section, when assembled in device 100, is generally situated within button activation assembly 200 (FIG. 1). Electrodes 142*a* and 142*b* are shown as individual traces separated by proximal assembly shaft component 169, which isolates the electrode traces 142*a*, 142*b* from one another. Electrodes 142*a* includes a proximal portion comprising a partial ring 300 extending at least partially circumferentially around proximal assembly shaft component 169. Likewise electrode 142*b* comprises a proximal portion comprising a ring 301 which may extend fully circumferentially around proximal assembly shaft component 169 as depicted in FIG. 10. Rings 300 and 301 provide contact surface area for electrical contacts such as clips 216*a*, 216*b* (FIGS. 12, 14).

Figure 11:
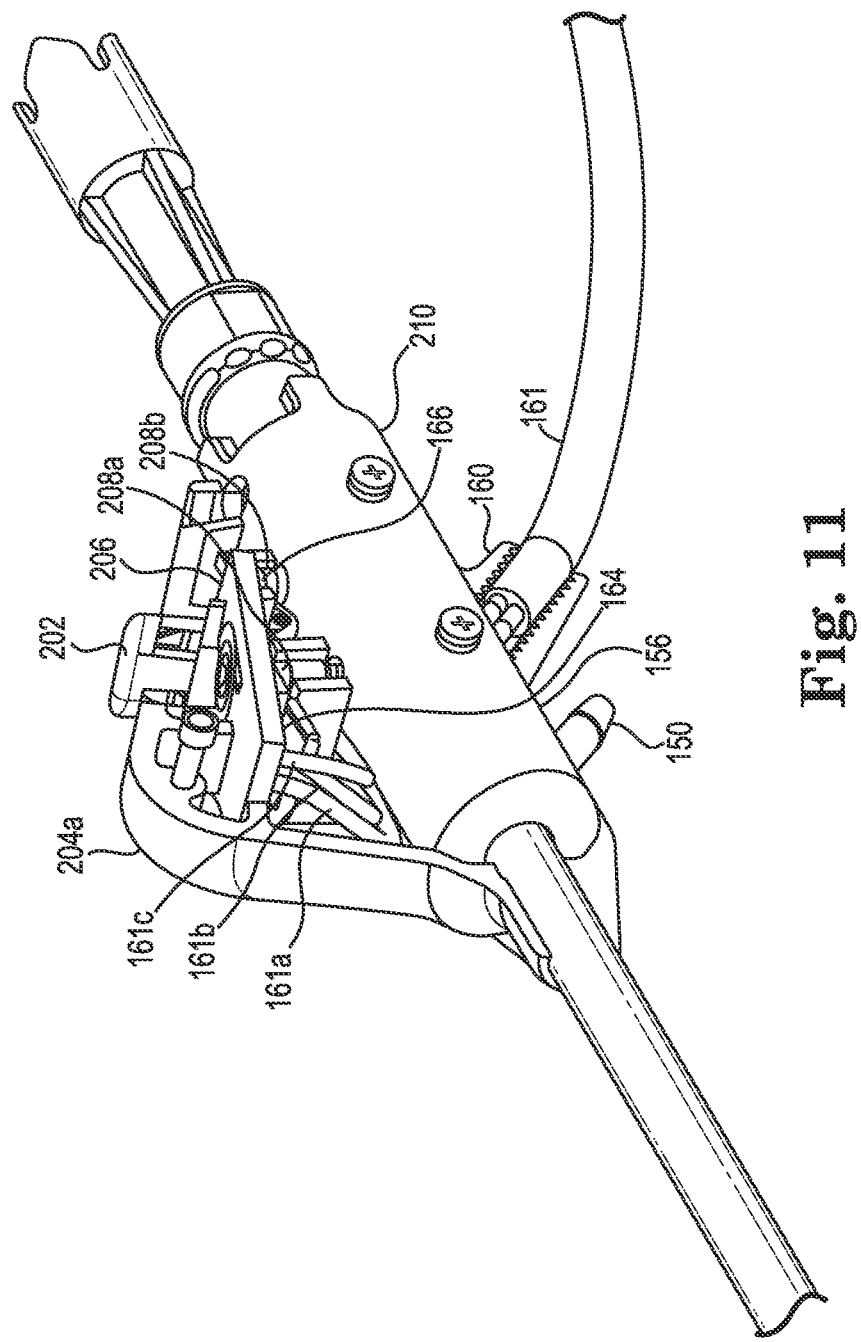
FIG. 11 is a perspective view of a proximal end of a device showing a button activation cell according to an aspect of the present invention.

FIGS. 11-14 depict the button activation assembly 200 and the way in which energy provided to electrodes 142*a*, 142*b*. FIG. 11 shows a partial cutaway view of the button activation assembly 200 one housing half 204*b* (FIG. 12) removed such that only housing half 204*a* is shown leaving portions of the button activation assembly 200 exposed. As shown in FIG. 11, at the proximal end region 110 of device 100 is provided a fluid housing 156 connected to the fluid connector 150 and an electrical contact housing 210 connected to the power source connector 160. The power source connector 160 is in turn coupled to a power cord or cable 161 comprising wires 161*a*, 161*b* and 161*c*. Power cord 161 is coupled to a printed circuit board (PCB) 206 via wires 161*a*, 161*b* and 161*c*. In addition, electrical contacts 164 and 166 electrically couple the power cord to caps 208*a* and 208*b*, as further explained with reference top FIGS. 12-14.

Figure 12:
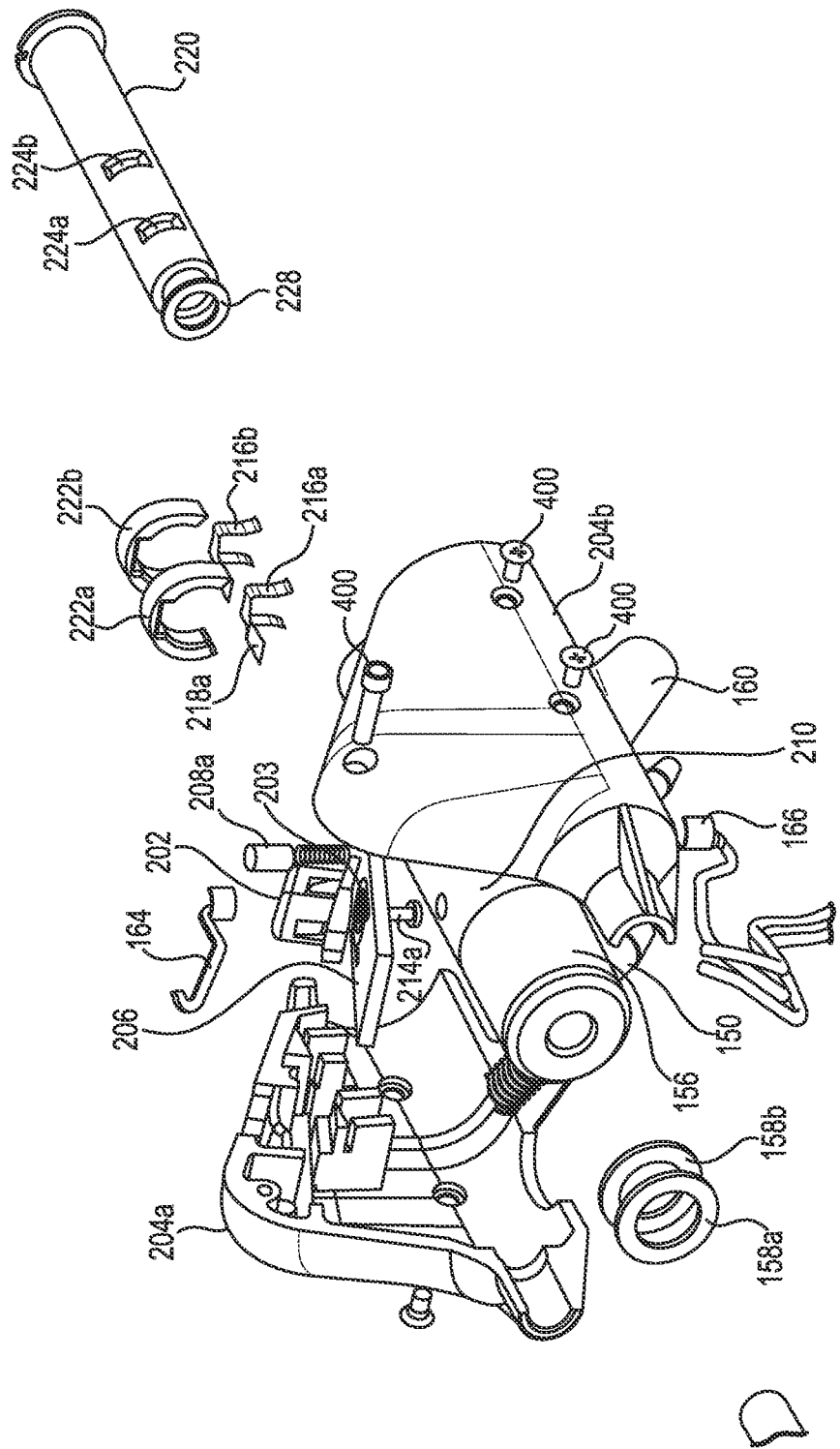
FIG. 12 is a an exploded view of the button activation cell of FIG. 11 according to an embodiment of the present invention.
Figure 13:
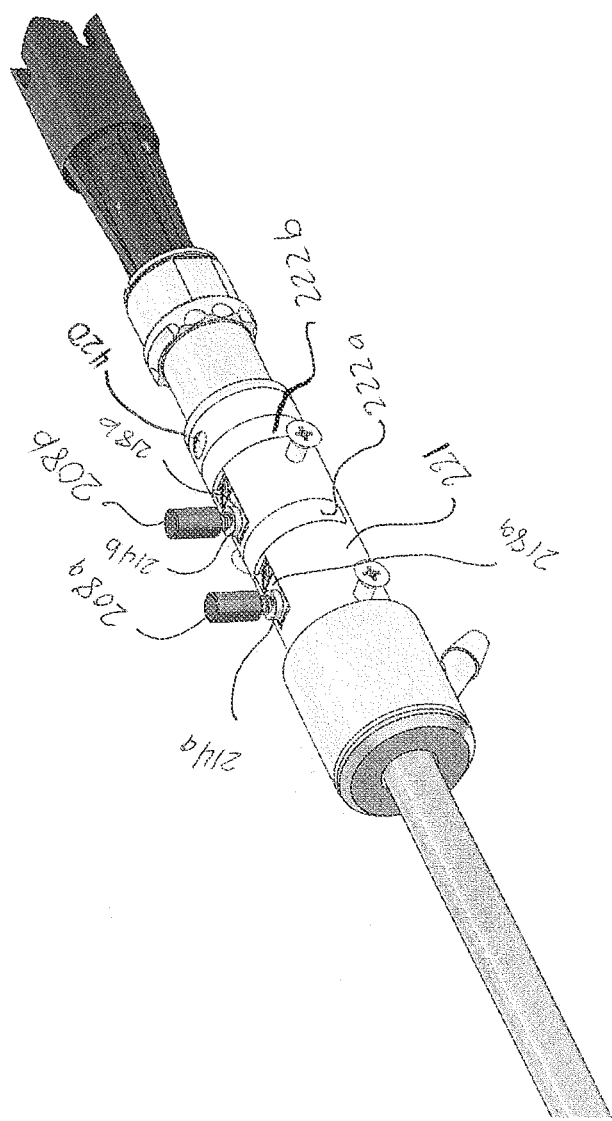
FIG. 13 is a perspective view of portions of the button activation cell of FIG. 11 according to an aspect of the present invention.

FIG. 12 shows and exploded view of the button activation cell 200 of FIG. 11 as well as a portion of proximal end region 110 with portions of the button activation cell removed. FIG. 13 shows an enlarged view of the portion of proximal end region 110 shown in FIG. 13 with still further portions removed. With reference between FIGS. 12-14, FIG. 12 shows two housing halves 204*a* and 204*b* which may be attached via any attachment device such as screws 400 and may, as described above, house various components of the button activation cell 200 as well as the fluid housing, electrical contact housing 210 and clip housing 220. Also depicted in FIG. 12 are o-rings 158*a*, 15*b* are adjacent fluid housing 156 and an o-ring 228 which is adjacent housing 220 for sealing fluid from the various components, including the electrical components provided in electrical contact housing 210.

Clip housing 220, shown alone or apart from cell 200 in FIG. 12, comprises two windows 224*a*, 224*b*. Clips 216*a* and 216*b* are provided in windows 224*a*, 224*b* with a flag 218*a*, 218*b* of each clip 216*a* and 216*b* viewable through or adjacent to windows 224*a*, 224*b*, such as depicted in assembled form in FIG. 13. Attached to clip housing 220 are two retaining rings 222*a*, 222*b*, for retaining the clips 216*a* and 216*b* in housing 220. As best seen in FIG. 14, post connectors 214*a*, 214*b* are coupled to clip flags 218*a*, 218*b* and provided on post connectors 214*a*, 214*b* are springs 212*a*, 212*b*. Over post connectors 214*a*, 214*b* and springs 212*a*, 212*b* are provided caps 208*a*, 208*b*. Also as best seen in FIG. 14, clips 216*a* and 216*b* are coupled to an in contact with rings 300 and 301 respectively of electrode traces 142*a*, 142*b*. Clips 216*a*, 216*b*, post connectors 214*a*,*b*, springs 212*a*, 212*b* and caps 208*a*, 208*b* are made of an electrically conductive material and provide electrical contact of the caps 208*a*, 208*b* to rings 300 and 301 when a source of power is activated or applied at caps 208*a*, 208*b*. As seen in FIGS. 11 and 12, the caps 208*a*, 208*b* are provided under the PCB 206, over which is provided button 202. Depressing button 202 drives a button contact assembly 203 which in turn moves to close circuitry of the PCB 206 allowing a pathway for current to flow from the power source 162 thus providing power to the electrodes 142*a*, 142*b* through the clips 216*a*, 216*b* as described above.

When energy is activated or applied to clips 216*a*, 216*b*, due to the intimate contact of clips 216*a* and 216*b* with electrode rings 300 and 301, electrical communication with bipolar electrodes 142*a*, 142*b* is achieved whereby energy is delivered along electrode traces 142*a* and 142*b* to the distal end 120 of device 100 and is applied to a targeted area of tissue as described herein above. This aspect of the present disclosure integrates electrodes 142*a* and 142*b* to the inner shaft 140 while isolating the inner shaft and electrodes 142*a* and 142*b* from other components and while distributing the required power to two separate and distinct electrodes 142*a*, 142*b*. This design also minimizes the number of layers required to make the distal end 120 of the device.

Figure 15:
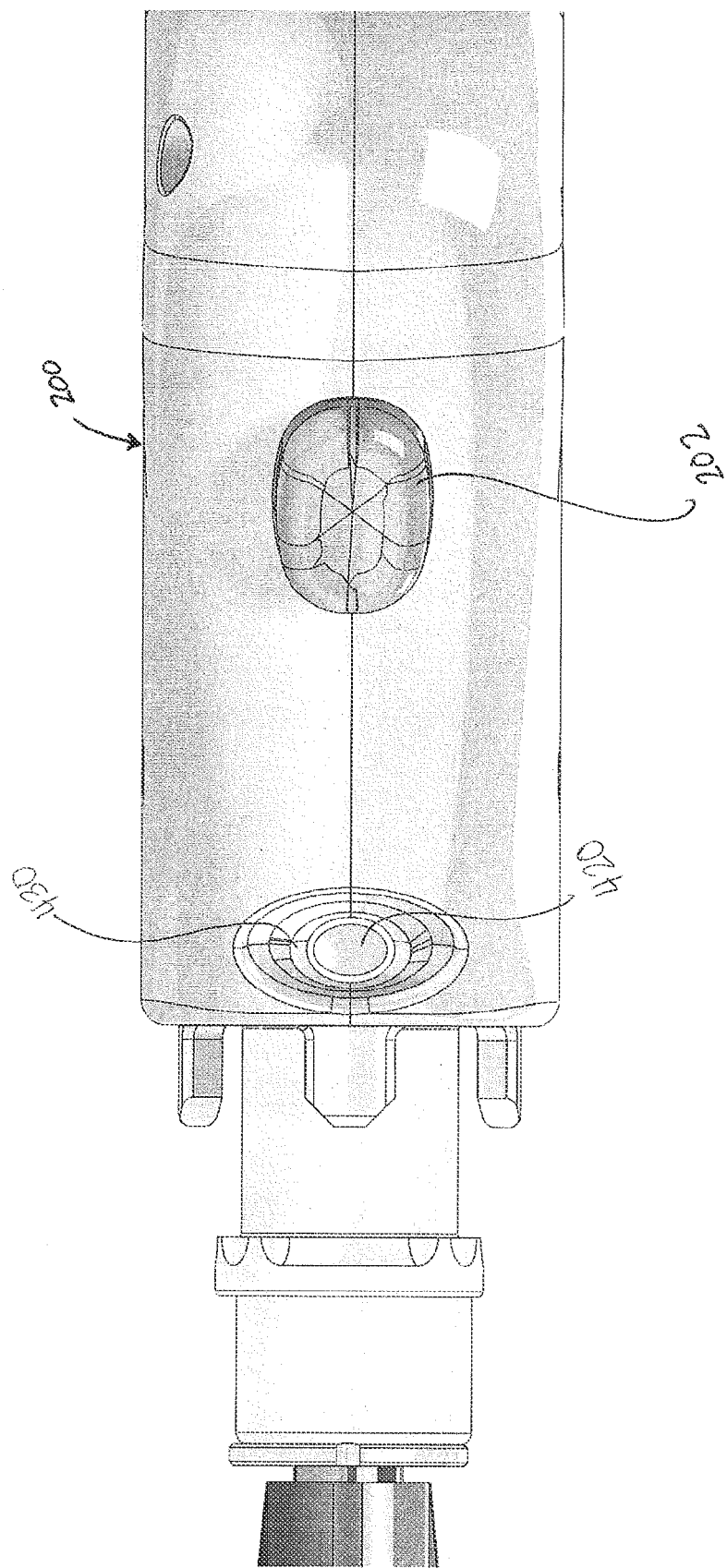
FIG. 15 is a top view of the button activation cell of FIG. 10 according to an aspect of the present invention.

FIG. 15 is a top view of the button activation assembly 200 and depicts an alignment fiducial 420 through a window 430 in housing 204. Alignment fiducial 420 is provided on housing 221 (FIG. 13). The alignment fiducial 420 is one of two fiducials which may be provided on device 100, with the second fiducial not shown. Alignment fiducials (e.g., 420) are provided as indicators of alignment of inner cutter 141 and may be colored to indicate a particular alignment configuration.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A bipolar electrosurgical debridement device comprising:
   a proximal region maintaining a housing;
   a distal region opposite the housing;
   an outer shaft defining a lumen and a distal end opposite the proximal region, wherein the distal end comprises an outer shaft cutter defining a window in the outer shaft;
   an inner shaft rotatably disposed within the lumen of the outer shaft, the inner shaft defining a distal portion opposite the proximal region, the inner shaft further including an inner shaft cutter, operatively associated with the outer shaft cutter and defining a cutting window in the inner shaft;
   a bipolar electrode assembly comprising first and second electrodes that are electrically isolated from one another, each electrode positioned at the distal region and electrically connected with a contact surface positioned at the proximal region within the housing;
   an indicator located remote from the distal region and associated with the housing to provide an indication of alignment of the inner shaft with respect to the outer shaft;
   a fluid source connector maintained by the housing and fluidly associated with the distal region; and
   a button activation assembly comprising:
      a button movable with respect to the housing to define an activation position;
      an electrical contact within the housing coupled with the button, wherein upon operation of the button to the activation position, electrical communication is afforded along an electrical pathway between a source of energy through each contact surface of the first and second electrodes to the distal region while the button is maintained in the activation position and wherein the electrical pathway is disconnected when the button is not in the activation position.

2. The debridement device of claim 1, wherein the electrical pathway between a source of energy through each contact surface of the first and second electrodes comprises a pair of resilient members.

3. The debridement device of claim 2, wherein the resilient members are located within the housing.

4. The debridement device of claim 3, wherein the resilient members comprise leaf springs.

5. The debridement device of claim 1, wherein the inner shaft cutter comprises a downward position when the inner shaft cutter is facing an inner wall of the outer shaft, wherein electrical communication between the source of energy through each contact surface of the first and second electrodes to the distal region is provided when the inner shaft cutter is in the downward position.

6. The debridement device of claim 5, wherein the inner shaft cutter is in the downward position in a hemostasis mode.

7. The debridement device of claim 1, wherein each contact surface is coupled with a spring positioned so as to maintain contact between the contact surface and the spring during rotation of the inner shaft relative to the outer shaft.

8. The debridement device of claim 1, wherein the button activation assembly includes first and second electrically conductive connections positioned within the housing, each electrically conductive connection in electrical communication with the button and a respective contact surface of the bipolar electrode assembly.

9. The debridement device of claim 1, wherein a location of the button relative to the housing defines an upper portion of the debridement device as a whole, and further wherein the window of the outer shaft faces the upper portion.

10. The debridement device of claim 1, wherein the button assembly further includes a printed circuit board disposed within the housing.

11. A bipolar electrosurgical debridement device comprising:
    a proximal region maintaining a housing;
    a distal region opposite the housing;
    an outer shaft defining a lumen and a distal end opposite the proximal region, wherein the distal end comprises an outer shaft cutter defining a window in the outer shaft;
    an inner shaft rotatably disposed within the lumen of the outer shaft, the inner shaft defining a distal portion opposite the proximal region, the inner shaft further including an inner shaft cutter, operatively associated with the outer shaft cutter and defining a cutting window in the inner shaft;
    an indicator located remote from the distal region and associated with the housing to provide an indication of alignment of the inner shaft with respect to the outer shaft;
    a bipolar electrode assembly comprising first and second electrodes that are electrically isolated from one another, each electrode positioned at the distal region and electrically connected with a contact surface positioned at the proximal region within the housing, wherein each contact surface is in electrical communication with a resilient member positioned so as to maintain contact between the contact surface and the resilient member during rotation of the inner shaft relative to the outer shaft;
    a fluid source connector maintained by the housing and fluidly associated with the distal region; and
    a button activation assembly comprising:
       a button movable with respect to the housing;
       an electrical contact coupled with the button, wherein upon operation of the button, electrical communication is provided between a source of energy through each contact surface and resilient member of the first and second electrodes to the distal region.

12. The debridement device of claim 11, wherein the button activation assembly includes first and second electrically conductive connections positioned within the housing, each electrically conductive connection in electrical communication with the button and a respective contact surface of the bipolar electrode assembly.

13. A bipolar electrosurgical debridement device comprising:
    a proximal region maintaining a housing;

a distal region opposite the housing;
an outer shaft defining a lumen and a distal end opposite the proximal region, wherein the distal end comprises an outer shaft cutter defining a window in the outer shaft;
an inner shaft rotatably disposed within the lumen of the outer shaft, the inner shaft defining a distal portion opposite the proximal region, the inner shaft further including an inner shaft cutter, operatively associated with the outer shaft cutter and defining a cutting window in the inner shaft;
an indicator positioned remote from the distal region and coupled to the housing to provide an indication of alignment of the inner shaft with respect to the outer shaft;
a bipolar electrode assembly comprising first and second electrodes that are electrically isolated from one another, each electrode positioned at the distal region and electrically connected with a contact surface positioned at the proximal region within the housing;
a fluid source connector maintained by the housing and fluidly associated with the distal region; and
a button activation assembly comprising:
    a button movable with respect to the housing;
    an electrical contact coupled with the button, wherein upon operation of the button, electrical communication is provided between a source of energy through each contact surface of the first and second electrodes to the distal region.

14. The debridement device of claim 13, wherein each contact surface is in electrical communication with a resilient member positioned so as to maintain contact between the contact surface and the resilient member during rotation of the inner shaft relative to the outer shaft.

15. A bipolar electrosurgical debridement device comprising:
a proximal region maintaining a housing;
a distal region opposite the housing;
an outer shaft defining a lumen and a distal end opposite the proximal region, wherein the distal end comprises an outer shaft cutter defining a window in the outer shaft;
an inner shaft rotatably disposed within the lumen of the outer shaft, the inner shaft defining a distal portion opposite the proximal region, the inner shaft further including an inner shaft cutter, operatively associated with the outer shaft cutter and defining a cutting window in the inner shaft;
an indicator positioned remote from the distal region and coupled to the housing, the indicator configured to provide an indication of alignment of the inner shaft with respect to the outer shaft;
a bipolar electrode assembly comprising first and second electrodes that are electrically isolated from one another, each electrode positioned at the distal region and electrically connected with a contact surface positioned at the proximal region within the housing;
a fluid source connector maintained by the housing and fluidly associated with the distal region; and
a button activation assembly comprising:
    first and second resilient members in electrical communication with the contact surface, the resilient members positioned so as to maintain contact between the contact surface and the corresponding resilient member during rotation of the inner shaft relative to the outer shaft;
    a button movable with respect to the housing to define an activation position;
    a printed circuit board disposed within the housing and operatively associated with the button;
    first and second electrically conductive connections positioned within the housing, each electrically conductive connection in electrical communication with the button and a respective one of the resilient members;
    an electrical contact within the housing coupled with the button, wherein upon manipulation of the button to the activation position, electrical communication is afforded along an electrical pathway between a source of energy through each of the resilient members and the contact surface of the first and second electrodes to the distal region while the button is maintained in the activation position and wherein the electrical pathway is disconnected when the button is not in the activation position.

* * * * *